(12) United States Patent
Roumpos

(10) Patent No.: US 7,132,084 B1
(45) Date of Patent: Nov. 7, 2006

(54) CANDLE WARMER

(75) Inventor: Deno N. Roumpos, Murray, UT (US)

(73) Assignee: Pende, Inc., Murray, UT (US)

( * ) Notice: Subject to any disclaimer, the term of this patent is extended or adjusted under 35 U.S.C. 154(b) by 14 days.

(21) Appl. No.: 09/876,606

(22) Filed: Jun. 7, 2001

(51) Int. Cl.
*A62B 7/08* (2006.01)
*F21V 33/00* (2006.01)
*H05B 11/00* (2006.01)
*F04B 53/00* (2006.01)
*F24H 3/02* (2006.01)

(52) U.S. Cl. .................. 422/125; 422/5; 422/123; 422/305; 422/306; 362/96; 362/253; 219/209; 219/220; 392/390; 416/146 R; 417/234; 126/110 D; 126/110 C

(58) Field of Classification Search .............. 422/5, 422/119, 124–125, 244, 305–307, 123; 239/55, 239/57, 60; 261/30, DIG. 88, DIG. 89; 416/146 R; 417/234; 126/110 C, 110 D; 431/289, 291; 165/80.3; 362/96, 253; 219/220, 209; 392/390
See application file for complete search history.

(56) References Cited

U.S. PATENT DOCUMENTS

| 2,668,993 | A | | 2/1954 | Bair |
| 3,630,697 | A | | 12/1971 | Duling |
| 3,890,085 | A | * | 6/1975 | Andeweg |
| 3,959,642 | A | * | 5/1976 | Turro ........................... 362/92 |
| 4,214,146 | A | | 7/1980 | Schimanski |
| 4,346,059 | A | | 8/1982 | Spector |
| 4,550,363 | A | * | 10/1985 | Sandell |
| 4,708,851 | A | * | 11/1987 | Freytag Von Loringhoven |
| 5,013,972 | A | * | 5/1991 | Malkieli et al. |
| 5,429,271 | A | | 7/1995 | Porter |
| 5,651,942 | A | * | 7/1997 | Christensen |
| 6,102,660 | A | * | 8/2000 | Lee |
| 6,106,786 | A | | 8/2000 | Akahoshi |
| 6,354,710 | B1 | * | 3/2002 | Nacouzi |
| 6,361,311 | B1 | * | 3/2002 | Smith |
| 6,413,476 | B1 | * | 7/2002 | Barnhart |

\* cited by examiner

Primary Examiner—Gladys J P Corcoran
Assistant Examiner—Monzer R. Chorbaji
(74) Attorney, Agent, or Firm—Thorpe North & Western LLP

(57) ABSTRACT

A scent dispersion system, comprising a heating device having a top surface, and a container of scented wax disposed upon the top surface of the heating device. Upon heating, scent from the wax is caused to disperse into the surrounding environment. The system may further comprise an air circulating fan associated with the heating device, for circulating air around the container of scented wax, to help disperse the scent.

7 Claims, 3 Drawing Sheets

US 7,132,084 B1

CANDLE WARMER

BACKGROUND OF THE INVENTION

1. Field of the Invention

The present invention relates generally to devices for dispersing scent throughout an area. More particularly, the present invention relates to a device for heating scented wax or candles to provide the benefits of scented candles without the problems that candles can create.

2. Related Art

Scented candles have enjoyed increasing popularity in recent years. They are available in a wide variety of pleasant scents, such as spices, herbs, and perfumes, and thus help to mask unpleasant odors and provide a desirable ambiance. They are also believed to provide some benefits through aroma therapy, such as relieving headaches, allergies, etc.

However, candles require a flame, and involve combustion. Consequently, they present a potential fire danger, and also disperse combustion products into the air, some of which may be toxic, such as carbon monoxide, plastics, and other noxious hydrocarbons. In a closed environment, such as a room, these combustion products can accumulate to hazardous levels, and with prolonged use, may lead to serious health problems. Moreover, the soot which accumulates with candle use is unattractive and increases the need for cleaning of walls, ceilings, etc.

SUMMARY OF THE INVENTION

It has been recognized that it would be advantageous to develop a device for dispersing scent throughout a room, which does not present the fire and pollutant dangers presented by burning scented candles.

It would also be desirable to have a device which allows the use of commonly available scented candles, and does not require specialized products for its use.

The invention advantageously provides a scent dispersion system, comprising a heating device having a top surface, and a container of scented wax disposed upon the top surface of the heating device, whereby, upon heating, scent from the wax is caused to disperse into a surrounding environment.

In accordance with a more detailed aspect of the present invention, the container of scented wax comprises a scented candle disposed in a glass jar, and the heating device is configured with heater controls for allowing selective adjustment of the temperature of heating of the container and the wax.

In accordance with an alternative aspect of the present invention, the system may include an air circulating fan associated with the heating device, for circulating air around the container of scented wax, to help disperse the scent into the surrounding environment.

Additional features and advantages of the invention will be apparent from the detailed description which follows, taken in conjunction with the accompanying drawings, which together illustrate, by way of example, features of the invention.

DETAILED DESCRIPTION

Figure 1:
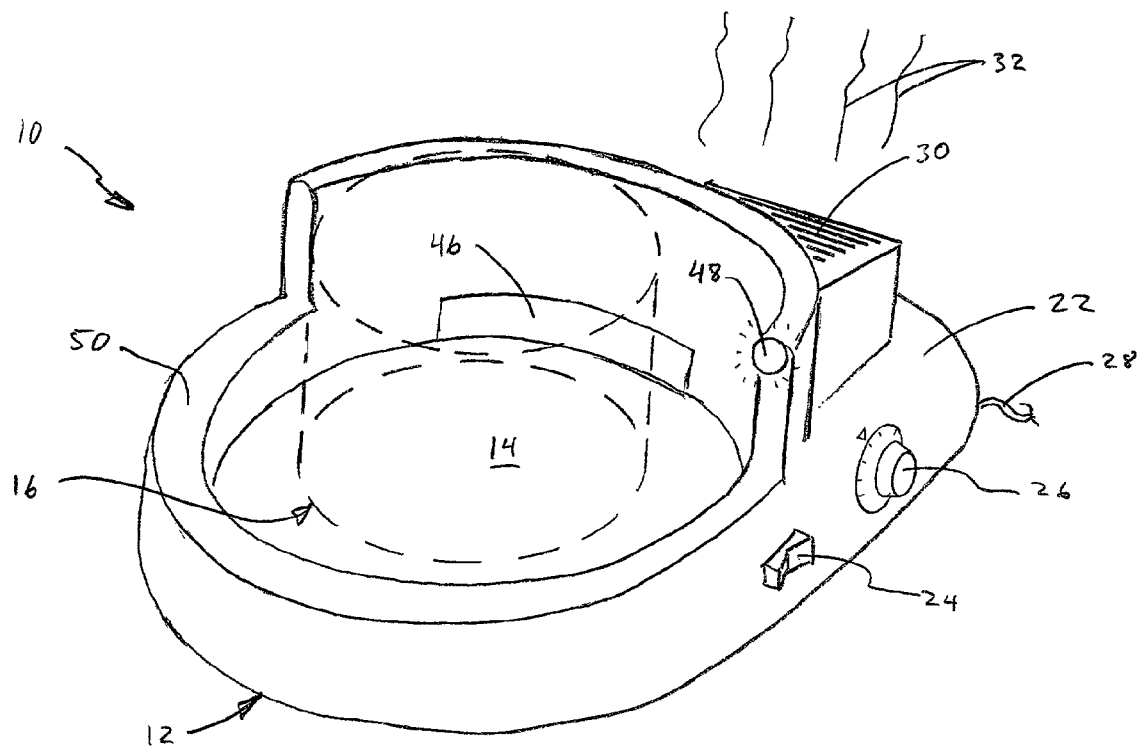
FIG. 1 is a perspective view of one embodiment of a candle warmer in accordance with the present invention.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

As illustrated in FIG. 1, a candle warmer in accordance with the present invention, indicated generally at 10, is shown for heating scented wax or a scented candle. As shown, the candle warmer 10 comprises a base unit 12, having a heat source 14, such as a heating plate, upon which a candle 16 (shown in dashed lines) may be placed. The heating plate is configured like a small hotplate or cup warmer. It will be apparent that, rather than a heating plate, an electrical heating coil may be used, similar to those on conventional electric ranges.

The candle 16 or warmer 10 includes a heat-resistant container (such as a glass jar) that contains scented wax, which may or may not include a wick. For example, many scented candles are originally contained in a jar. However, others are not. Accordingly, if the heat resistant container is associated with the candle warmer, a user is free to use candles or scented wax which do not come prepackaged in a container.

In use, the heating plate heats the wax, causing it to melt, and then slowly evaporate and disperse scent into the surrounding area, such as a room, etc. While scented wax may release some scent at room temperature, and more scent as its temperature approaches a melting point, it will be apparent that a significant quantity of scent is generally not released until the wax is at least partially melted.

The base unit 12 generally comprises a housing 22, which encloses the electrical components for providing power to the heating plate. The device may include, disposed upon the housing, controls for the device, including an on/off switch 24 and a temperature control knob 26. These controls allow a user to switch the unit on and off, and allow control of the temperature of the heating plate 14. By manipulating the temperature control knob, the user can control the rate of evaporation of the wax, and thus control the strength of the scent and the longevity of the candle. Additional controls and/or control circuitry may also be associated with the base unit. For example, the base unit may include a timer circuit for turning the unit on and off, and for automatically adjusting the temperature of the heating plate. The timer circuit may be configured to cause the device to operate only during specified hours of the day.

The candle warmer may also be configured with a timer circuit to cause the heating plate to reach an initial heated temperature and hold that temperature to melt the wax, then, after a specified time, reduce the temperature to simply maintain the melted state. For example, the inventor has found that with a candle warmer which uses 48 watts of power, a 6 ounce candle will melt in about 20 minutes. A 24 watt candle warmer will take about one hour to melt the same candle. However, once melted, far less power is required to maintain the melted state.

A power supply cord 28 connects the device to a source of electrical power, typically an electrical outlet providing conventional 110 v AC power. The controls may be simplified from that shown in FIG. 1. For example, the candle warmer may not include a temperature control knob, but simply operate at a preset temperature/power setting. Additionally, rather than an on/off switch, powering of the unit may simply be controlled by connecting or disconnecting the power supply cord to the power supply.

For better dispersion of the scent, an air circulation fan (not visible in FIG. 1) may be disposed within the housing 22 of the base unit 12 below a grate 30. The fan may blow air upward, as indicated by flow lines 32, to assist in circulating the scent throughout the surrounding room or area. A separate fan control switch (not shown) may be provided to allow independent control of the fan, or the fan may be configured to continuously operate when the candle warmer is in use.

Figure 2:
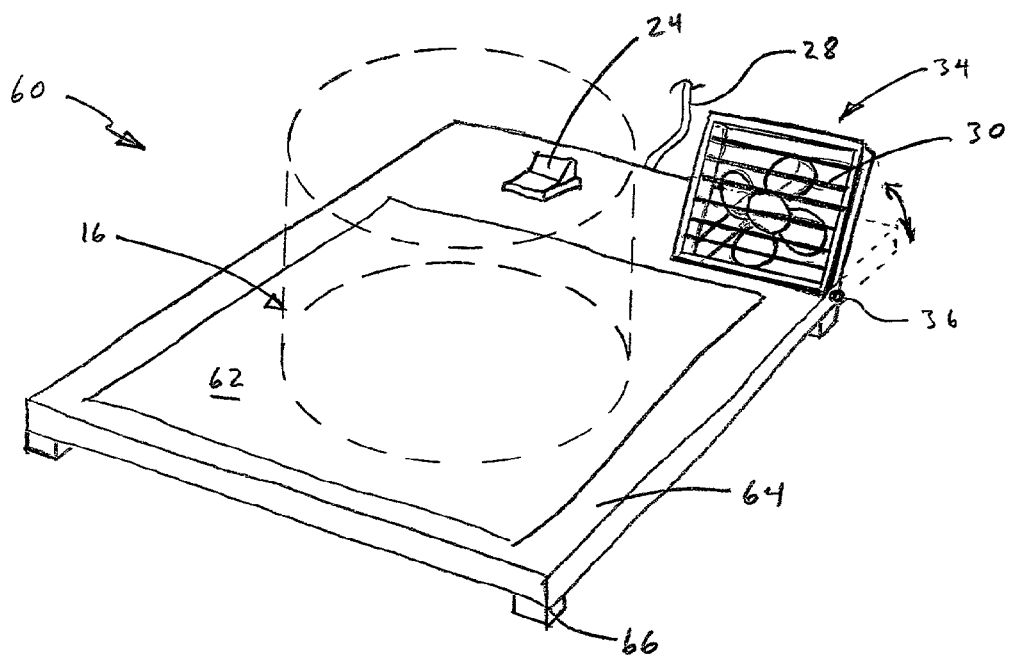
FIG. 2 is a perspective view of an alternative embodiment of a candle warmer in accordance with the present invention.
Figure 5:
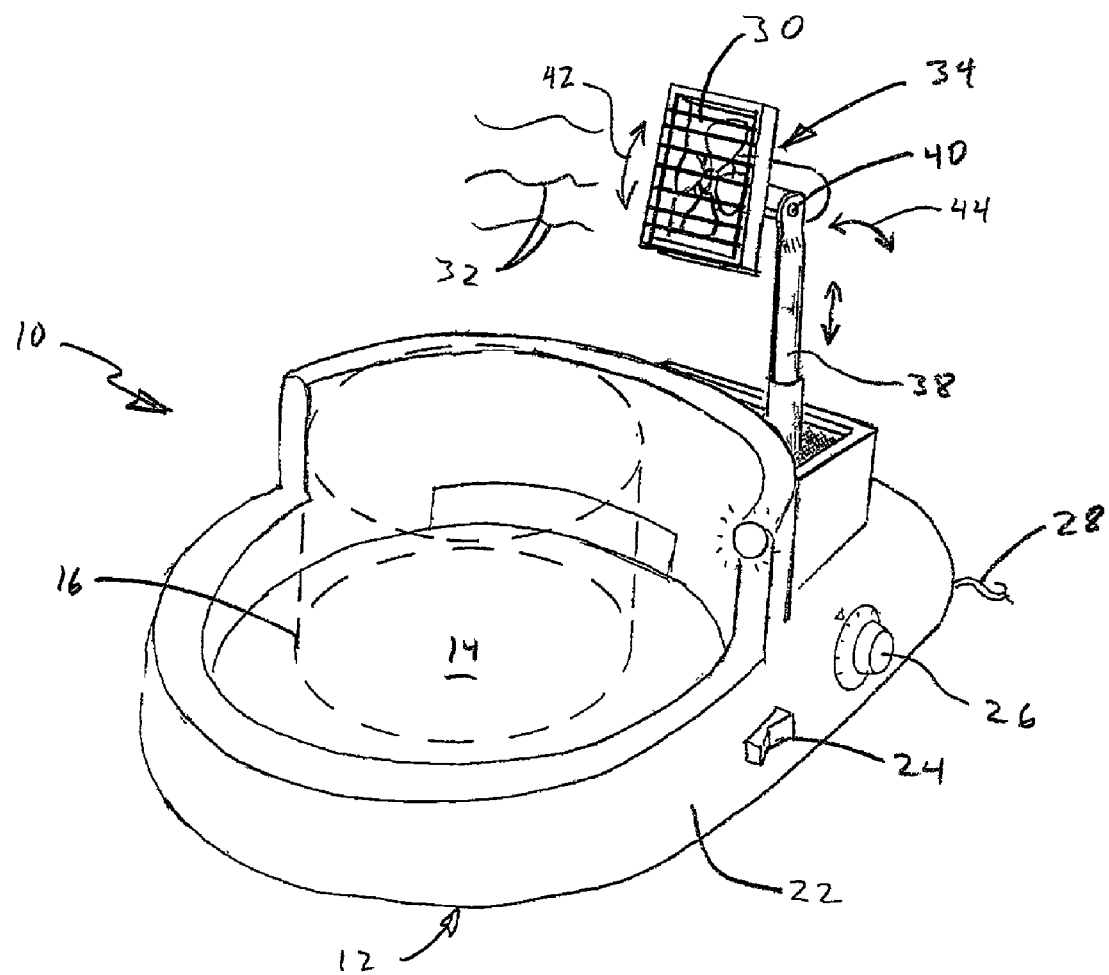
FIG. 5 is a perspective view of the candle warmer of FIG. 1, having the air circulating fan mounted on a telescoping rod.

One embodiment of an air circulation fan 34 is shown in FIG. 2. The fan 34 is disposed behind the grate 30, and the entire fan assembly may be configured to rotate on a hinge 36 to allow the orientation of the fan to be adjusted, thereby allowing better circulation of the aroma of the candle. Alternatively, referring to FIG. 5, the fan assembly 34 and the grate 30 may be moveably disposed on a telescoping rod 38. The telescoping rod allows the fan assembly 34 to be raised out of the housing 22 to a desired height above the base, and aimed in various ways. The fan can be pivoted up and down on a pivot connection 40, in the direction of arrow 42, and may be rotated side-to-side about the axis of the rod 38, as indicated by arrow 44. When the candle warmer is not in use, the fan may be pushed downward into a retracted position in the base housing 22, to resume the appearance of the device as shown in FIG. 1. It will be apparent that any of the various embodiments of the fan may be associated with any of the various depicted embodiments of the candle warmer device as a whole.

The candle warmer may include various devices to improve its appearance and perhaps use a light source to simulate some of the effects of a burning candle, if desired. For example, referring again to FIG. 1, a glow tube 46 may be disposed adjacent to the heating plate 14, and in a location which is behind the candle. The glow tube is a commercially available item which comprises a section of illumination tubing with a light bulb at one end, and provides a steady glow behind the candle to help provide a glowing ambiance. It will be apparent that the color of the glow tube may be selected as desired. The unit may also include a flicker light 48, which is a small incandescent electric bulb which provides the flickering effect of a burning candle.

The embodiment of the candle warmer depicted in FIG. 1 is configured with a 4¼" diameter heating plate with a rim 50 therearound to help hold the candle on the heating plate 14. However, the heating plate need not be round, as shown in FIG. 2. In this alternative embodiment, the candle warmer 60 includes a rectangular heating plate 62 supported on a rectangular base 64, which has feet 66 for supporting it upon a table or other surface. The base also includes the on-off switch 24, and supports the fan assembly 34. It will also be apparent that non-cylindrical candles (not shown) may be used with any of the embodiments of the candle warmer 10.

Figure 3:
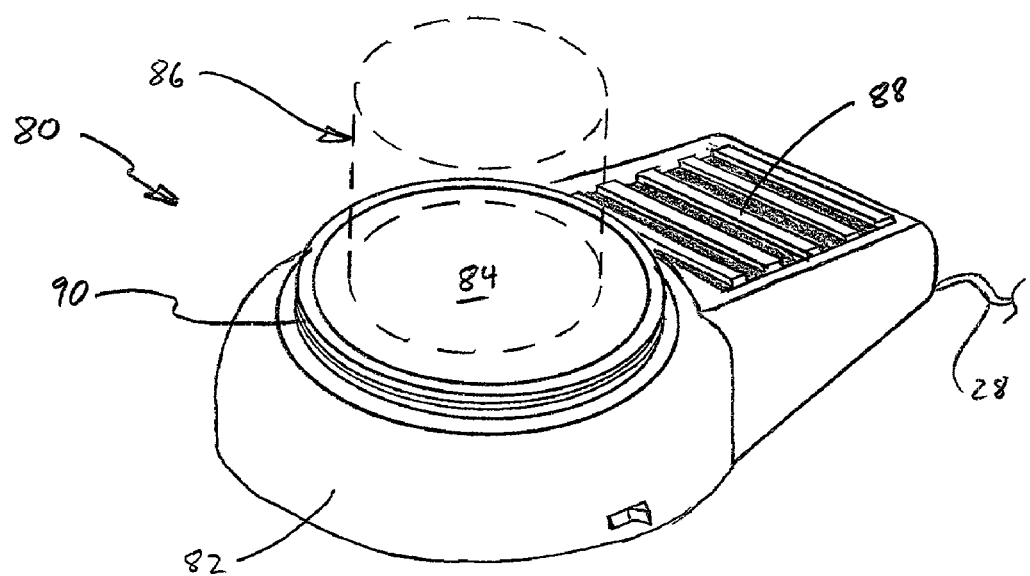
FIG. 3 is a perspective view of yet another alternative embodiment of a candle warmer in accordance with the present invention.
Figure 4:
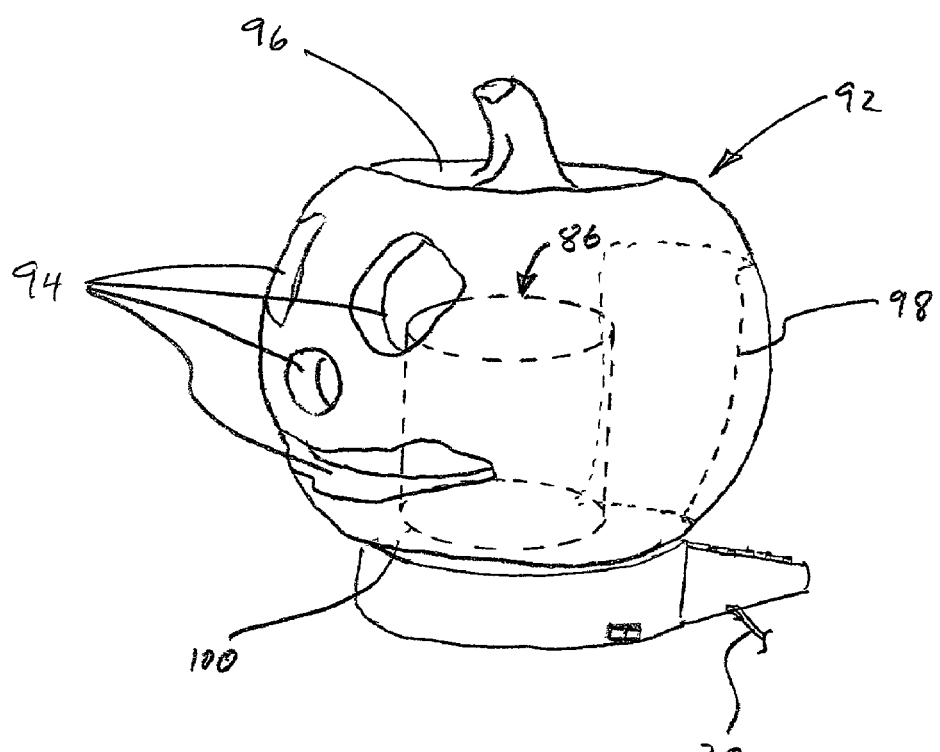
FIG. 4 is a perspective view of the candle warmer of FIG. 3, having a candle cover disposed thereon.

Referring to FIGS. 3 and 4, in yet another alternative embodiment, a candle warmer 80, having a base 82 and heating plate 84, is configured to heat a candle 86. An air circulating fan, as described above, is disposed in the base 82 behind a grate 88, and may be a moveable fan as explained above. Disposed around the heating plate 84 is a threaded rim 90, which is configured to receive a cover 92, shown in FIG. 4, which surrounds the candle. The cover includes openings 94 for allowing heat and scent to escape, which may be configured in any desired manner, preferably consistent with the appearance of the cover. For example, as shown in FIG. 4, a Jack-o-lantern cover may include openings which comprise a simulated carved Jack-o-lantern face. Other openings may also be provided in or near the top of the cover.

The top of the cover 92 may include a removable lid 96, as is consistent with the Jack-o-lantern configuration, the lid providing access to a candle access opening which allows easy insertion or removal of the candle 86. Alternatively, the cover may include candle access opening 98 (shown outlined in dashed lines) formed in the back of the cover, to allow insertion or removal of the candle from the back side.

The cover 92 is preferably made of injection molded plastic, and may take any desired decorative form or novelty shape. For example, covers may have forms which correspond to holidays (e.g., a Christmas tree, a turkey, etc.), hobbies or leisure time activities (e.g., a golf ball, a basketball, a baseball, a tennis ball, dice, an animal, a football, a slot machine, etc.), or any other interesting shape or form (e.g. an automobile, an airplane, a trophy, a sculpture, etc.). Disposed on a bottom rim 100 of the cover are interior threads (not shown) which mate with the threads on the rim 90 of the base. This configuration allows the cover to be quickly and easily interchanged as desired. One cover may be easily removed, and another screwed on in its place. It will be apparent, however, that other methods of connection of the cover to the base may be used, such as clips, tabs, a press fit, etc. Any method which mechanically connects the cover to the base and adequately holds it in proper orientation will be suitable.

The embodiment of FIGS. 3 and 4 may be smaller than the other embodiments shown, having a 2¾" diameter heating plate, and configured to heat relatively small candles. Accordingly, this embodiment of the candle warmer is less obtrusive, and takes up less space in a home or office. The cover may also serve the function of disguising the device.

The inventor has found that with this invention a scented candle will last much longer than if burned in the conventional manner. For example, the inventor has found that a typical scented candle which if burned will last for 40 to 60 hours, will provide more than 3500 hours of scent when used in combination with the present invention. The candle warmer 10 thus economically provides the benefits of scented candles, without the dangers or inconvenience associated with open flames, and the soot or residue that candles can create.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A candle warmer, comprising:
   a container of scented wax;
   a base;
   a heating device associated with the base, the heating device having a top surface configured to receive the container of scented wax thereon;
   means for activating the heating device, disposed on the base, whereby scent from the container of scented wax may be caused to disperse into a surrounding environment;
   means for varying the temperature of the heating device, disposed on the base, to enable an operator to vary the temperature of the scented wax;
   wherein a total height of the low-profile base is less than half a total height of the container of scented wax;
   an air circulating fan attached to the base, and configured to circulate air in the vicinity of the heating device;
   wherein the location and orientation of the air circulating fan are adjustable with respect to the base;
   a telescoping rod, configured to extend upwardly from the base; and
   a pivotal connection between the air circulating fan and a top of the telescoping rod, such that the fan may be raised to a position above the base.

2. The candle warmer according to claim 1, further comprising a decorative cover configured to attach to the base, whereby the heating device and the container of scented wax disposed thereon may be enclosed, the cover including at least one opening for allowing escape of scent from within the cover.

3. The candle warmer according to claim 2, wherein the decorative cover further comprises a candle access opening to allow insertion or removal of a candle from within the container without removing the cover from the base.

4. The candle warmer of claim 2, wherein the decorative cover comprises a decorative enclosure having a form selected from the group consisting of a Christmas tree, a turkey, a Jack-o-lantern, a golf ball, a basketball, a football, a baseball, a tennis ball, an animal, a slot machine, dice, an airplane, an automobile, a trophy, and a sculpture.

5. The candle warmer of claim 1, further comprising a flickering light source associated with the candle warmer and being configured to simulate the appearance of a burning candle.

6. The candle warmer according to claim 1, wherein substantially all of the operable components of the candle warmer are disposed below the container of scented wax.

7. The candle warmer of claim 1, wherein the container of scented wax comprises a scented candle.

* * * * *